(12) United States Patent
Sigg et al.

(10) Patent No.: US 8,076,305 B2
(45) Date of Patent: Dec. 13, 2011

(54) BIOLOGICAL PACEMAKERS INCLUDING MUTATED HYPERPOLARIZATION-ACTIVATED CYCLIC NUCLEOTIDE-GATED (HCN) CHANNELS

(75) Inventors: Daniel C. Sigg, St. Paul, MN (US); Vinod Sharma, Blaine, MN (US); Yong-Fu Xiao, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1364 days.

(21) Appl. No.: 11/565,433

(22) Filed: Nov. 30, 2006

(65) Prior Publication Data

US 2009/0099611 A1 Apr. 16, 2009

(51) Int. Cl.
*A61K 48/00* (2006.01)
*A01N 63/00* (2006.01)
*C12N 15/74* (2006.01)
*C07H 21/04* (2006.01)

(52) U.S. Cl. .................. 514/44 R; 424/93.2; 424/93.21; 536/23.1; 435/320.1

(58) Field of Classification Search .................. None
See application file for complete search history.

(56) References Cited

U.S. PATENT DOCUMENTS

| | | | |
|---|---|---|---|
| 6,718,204 B2 | 4/2004 | DeGroot et al. | |
| 6,892,094 B2 | 5/2005 | Ousdigian et al. | |
| 6,922,585 B2 | 7/2005 | Zhou et al. | |
| 7,107,098 B2 | 9/2006 | Sharma et al. | |
| 7,142,928 B2 | 11/2006 | Sharma et al. | |
| 7,149,577 B2 | 12/2006 | Sharma et al. | |
| 7,177,680 B2 | 2/2007 | Sharma et al. | |
| 7,190,993 B2 | 3/2007 | Sharma et al. | |
| 7,392,082 B2 | 6/2008 | Sharma | |
| 7,415,307 B2 | 8/2008 | Sharma et al. | |
| 7,515,960 B2 | 4/2009 | Sharma | |
| 7,608,458 B2 | 10/2009 | Soykan et al. | |
| 7,622,303 B2 | 11/2009 | Soykan et al. | |
| 7,778,705 B2 | 8/2010 | Sigg et al. | |
| 7,894,899 B2 | 2/2011 | Sharma | |
| 2004/0181259 A1 | 9/2004 | DeGroot et al. | |
| 2004/0214182 A1 | 10/2004 | Sharma et al. | |
| 2004/0215251 A1 | 10/2004 | Sharma et al. | |
| 2004/0254134 A1* | 12/2004 | Marban et al. | 514/44 |
| 2005/0021089 A1 | 1/2005 | Sharma | |
| 2006/0020316 A1 | 1/2006 | Martinez et al. | |
| 2006/0088503 A1 | 4/2006 | Sharma et al. | |
| 2006/0247697 A1 | 11/2006 | Sharma et al. | |
| 2007/0021375 A1 | 1/2007 | Sharma et al. | |
| 2007/0087033 A1 | 4/2007 | Sigg et al. | |
| 2007/0156189 A1 | 7/2007 | DeGroot et al. | |
| 2007/0218034 A1 | 9/2007 | Sigg et al. | |
| 2008/0103537 A1 | 5/2008 | Sigg et al. | |
| 2008/0200769 A1 | 8/2008 | Sharma et al. | |
| 2009/0099611 A1 | 4/2009 | Sigg et al. | |
| 2009/0157129 A1 | 6/2009 | Sharma | |
| 2009/0233990 A1 | 9/2009 | Cho et al. | |
| 2010/0047915 A1 | 2/2010 | Soykan et al. | |
| 2010/0076063 A1 | 3/2010 | Sharma et al. | |

FOREIGN PATENT DOCUMENTS

| | | |
|---|---|---|
| WO | WO 02/098286 A2 | 12/2002 |
| WO | WO 02/098286 A3 | 5/2003 |
| WO | W02004065580 A | 8/2004 |
| WO | W02005062958 A | 7/2005 |

OTHER PUBLICATIONS

Stieber et al. J Biol Chem 2003;278:33672-80.*
Bucchi et al. Circulation Aug. 2006:114:992-9.*
Proenza et al. J Biol Chem 2002;277:29634-42.*
Tsang et al, "Dissecting the Structural and Functional Roles of the S3-S4 Linker of Pacemaker (hyperpolarization-activated Cyclic Nucleotide-modulate) Channels by Systemaivc length Alterations" J. Biol. Chem., vol. 279, No. 42, 2004, pp. 43752-43759.
Henrikson et al, "Identification of a Surface Charged Residue in the S2-S4 Linker of the Pacemaker (HCN) Channel the Influences Activation Gating" J. Biol. chem., vol. 278, No. 16, 2003, pp. 13647-13654.
Lesso et al, "Helical Secondary Structure of the External S3-S4 Linker of Pacemaker (HCN) channels Revealed by Site-Dependent Perturbations of Activation Phenotype", J. Biol. Chem., vol. 278, No. 25, 2004, pp. 22290-22297.
International Search Report, PCT/US2007/085576, Nov. 7, 2008, 9 Pages.
Baruscotti et al., "Physiology and pharmacology of the cardiac ("funny") current," 2005 *Parmacol. Therap.* 107:59-79.
Bell et al., "Changes in local S4 environment provide a voltage-sensing mechanism for mammalian hyperpolarization-activated HCN channels," Jan. 2004 *J. Gen. Physiol.* 123:5-19.
Chandler et al., "Molecular architecture of the human sinus node: insights into the function of the cardiac pacemaker," 2009 *Circulation* 119:1562-1575. Including 33 pages of Supplemental Material.
Chen et al., "The S4-S5 linker couples voltage sensing and activation of pacemaker channels," Sep. 25, 2001 *Proc. Natl. Acad Sci. USA* 98:11277-11282. Available online on Sep. 11, 2001.
Chen et al., "Voltage sensor movement and cAMP binding allosterically regulate an inherently voltage-independent closed-open transition in HCN channels," Feb. 2007 *J. Gen Physiol.* 129:175-188. Published on Jan. 19, 2007.
Dobrzynski et al., "New insights into pacemaker activity: promoting understanding of sick sinus syndrome," 2007 *Circulation* 115:1921-1932.
Fedorov et al., "Postganglionic nerve stimulation induces temporal inhibition of excitability in rabbit sinoatrial node," 2006 *Am. J Physiol. Heart Circ. Physiol.* 291:H612-H623. Published on Mar. 24, 2006.
Geerts et al., "Characterization of the normal cardiac myofiber field in goat measured with MR-diffusion tensor imaging," 2002 *Am. J. Physiol. Heart Circ. Physiol.* 283:H139-H145. Published on Feb. 28, 2002.

(Continued)

*Primary Examiner* — Q. Janice Li (57) ABSTRACT

A composition for implantation into cardiac tissue includes a biological pacemaker that, when implanted, expresses an effective amount of a mutated hyperpolarization-activated and cyclic nucleotide-gated (HCN) isoform to modify $I_h$ when compared with wild-type HCN. Methods for implementing each of the biologocal pacemakers include implanting each of biologocal pacemakers into cardiac tissue.

40 Claims, 4 Drawing Sheets

OTHER PUBLICATIONS

Ishii et al., "Tryptophan-scanning mutagenesis in the S1 domain of mammalian HCN channel reveals critical for voltage-gated activation," 2007 J. Physiol. 579:291-301. Available online on Dec. 21, 2006.

Jaye et al., "Ventricular Biological Pacemaker Successfully Created in Canine Model by Human HCN4 Gene Transfer," Meeting Abstract 21428; presented at *Scientific Sessions 2010*; Nov. 14-16: Chicago, IL. American Heart Association. Published in Nov. 23, 2010 *Circulation* 122(21—supplement):A21428. Available online [retrieved on Dec. 21, 2010].

Kashiwakura et al., "Gene transfer of a synthetic pacemaker channel into the heart. A novel strategy for biological pacing," 2006 *Circulation* 114:1682-1686. Available online on Oct. 9, 2006.

Katz et al., "Cardiac gene therapy: optimization of gene delivery techniques in vivo," Apr. 2010 *Hum. Gene Ther.* 21:371-380.

Lesso and Li, "Helical secondary structure of the external S3-S4 linker of pacemaker (HCN) channels revealed by site-dependent perturbations of activation phenotype," Jun. 20, 2003 *J. Biol. Chem.* 278:22290-22297. Available online on Mar. 31, 2003.

Monks et al., Helical structure and packing orientation of the S2 segment in the *Shaker* K+channel, Mar. 1999 *J. Gen. Physiol.* 113:415-423. Published on Mar. 1, 1999.

Nikolskaya and Sharma, "Modulating cellular electrophysiology with exogenous ion channel expression can trigger unexpected cellular remodeling," May 2009 *Molecular Therapy* 17(Supp 1):S352, Abstract No. 921. Meeting program of the *12th Annual Meeting of the American Society of Gene Therapy*: San Diego, CA; May 27-30, 2009.

Nikolskaya and Sharma, "Modulating cellular electrophysiology with exogenous ion channel expression can trigger unexpected cellular remodeling," Poster presented at the *12th Annual Meeting of the American Society of Gene Therapy*: San Diego, CA; May 30, 2009.

Plotnikov et al., "Biological pacemaker implanted in canine left bundle branch provides ventricular escape rhythms that have physiologically acceptable rates," 2004 *Circulation* 109:506-512. Available online on Jan. 20, 2004.

Qu et al., "Expression and function of a biological pacemaker in canine heart," 2003 *Circulation* 107:1106-1109.

Rosen et al., "Genes, stem cells and biological pacemakers," 2004 *Cardiovasc. Res.* 64:12-23.

Rosen et al., "Recreating the biological pacemaker," 2004 *Anatom. Rec. Part A* 280A:1046-1052. Available online on Sep. 15, 2004.

Rosen, "Conference report: building a biological pacemaker." Author manuscript available online on Nov. 1, 2008, at the National Institutes of Health PubMed Central website. Also published in final edited form in 2007 J. *Electrocardiol.* 40(Supp):S197-S198.

Scollan et al., "Reconstruction of cardiac ventricular geometry and fiber orientation using magnetic resonance imaging." Author manuscript available online on Jun. 1, 2006, at the National Institutes of Health PubMed Central website. Available online. Also published in final edited form in Aug. 2000 Ann. Biomed. Eng. 28:934-944.

Thollon et al., "Use-dependent inhibition of hHCN4 by ivabradine and relationship with reduction in pacemaker activity," 2007 *British J. Pharmacol.* 150:37-46. Available online on Nov. 27, 2006.

Tse et al., "Bioartificial sinus node constructed via in vivo gene transfer of an engineered pacemaker HCN channel reduces the dependence of electronic pacemaker in a sick-sinus syndrome model," 2006 *Circulation* 114:1000-1011. Available online on Aug. 21, 2006.

Vaca et al., "Mutations in the S4 domain of a pacemaker channel alter its voltage dependence," 2000 *FEBS Letters* 479:35-40.

Viswanathan et al., "Recreating an artificial biological pacemaker: insights from a theoretical model," Jul. 2006 *Heart Rhythm* 3(7):824-831. Available online on Mar. 16, 2006.

Wu et al., "Study of myocardial fiber pathway using magnetic resonance diffusion tensor imaging," Sep. 2007 *Magn. Reson. Imaging* 25:1048-1057. Available online on Mar. 23, 2007.

Xiao and Sigg, "Biological approaches to generating cardiac biopacemaker for bradycardia," Oct. 25, 2007 *Acta Physiologica Sinica* 59:562-570.

Xiao et al., "Hysteresis in human HCN4 channels: a crucial feature potentially affecting sinoatrial node pacemaking," Feb. 25, 2010 *Acta Physiologica Sinica* 62:1-13.

Zeng et al., "AAV1-HCN4-mediated Biological Pacemaker Paces the Canine Heart with AV Bock over 7 Months and Responds Well to Autonomic Challenges," Meeting Abstract 18147; presented at *Scientific Sessions 2010*; Nov. 14-16: Chicago, IL. American Heart Association. Published in Nov. 23, 2010 *Circulation* 122(21-supplement):A18147. Available online [retrieved on Apr. 25, 2011].

Greener et al., "Molecular architecture of the human specialized atrioventricular conduction axis," *J Mol. Cell Cardiol.*, Apr. 2011; 50:642-651. Available online on Jan. 21, 2011.

Reese et al., "Imaging Myocardial Fiber Architecture in Vivo with Magnetic Resonance," *Magn. Reson. Med.*, Dec. 1995; 34(6):786-791.

Sharma et al., "Direct measurements of membrane time constant during defibrillation strength shocks," *Heart Rhythm*, Apr. 2007; 4(4):478-486. Available online on Dec. 15, 2006.

Sharma et al., "Incidence and Characteristics of Type-2 Breaks in Response to Antitachycardia Pacing Therapy in Implantable Cardioverter Defibrillator Patients," *J. Cardiovasc. Electrophysiol.*, Nov. 2003; 14(11):1156-1162.

Xie et al., "So Little Source, So Much Sink: Requirements for Afterdepolarizations to Propagate in Tissue," *Biophys. J.*, Sep. 8, 2010; 99:1408-1415.

\* cited by examiner

BIOLOGICAL PACEMAKERS INCLUDING MUTATED HYPERPOLARIZATION-ACTIVATED CYCLIC NUCLEOTIDE-GATED (HCN) CHANNELS

FIELD OF THE INVENTION

The present invention relates to curative therapy for cardiac dysfunction, and, more particularly, to introduction of biological curative therapeutic agents to treat arrhythmias and cardiac pacing dysfunction.

BACKGROUND OF THE INVENTION

Cardiac contraction in a healthy human heart is initiated by spontaneous excitation of the sinoatrial ("SA") node, which is located in the right atrium. The electric impulse generated by the SA node travels to the atrioventricular ("AV") node where it is transmitted to the bundle of His and to the Purkinje network. The fibers in the Purkinje network branch out in many directions to facilitate coordinated contraction of the left and right ventricles. In some disease states, the heart loses some of its natural capacity to pace properly. Such dysfunction is commonly treated by implanting a pacemaker.

While effectively improving the lives of many patients, implantable pacemakers have certain technical limitations. For example, implantable pacemakers rely on a self-contained power source such as a battery and consequently have a limited lifetime before the power source is in need of replacement. Hence, an otherwise healthy patient may require multiple surgeries to replace the power source or the entire implantable pacemaker. Also, implantable pacemakers may not directly respond to physiological signals similar to the way the SA node responds to such signals.

Recently, biological methods of influencing a patient's cardiac cells have been developed, some of which include administering biopharmaceutical compositions that affect cardiac pacing. Developments in genetic engineering have produced methods for genetically modifying cardiac cells to modify non-pacemaking cardiac cells to cardiac cells or regenerates the pacing capabilities of cells in the conduction system of the heart. For example, U.S. Pat. No. 6,214,620 describes a method for modulating the excitability of ventricular cells by controlling the regulation of the expression of certain ion channels (e.g. $K^+$ channels). PCT Publication No. WO 02/087419 and WO 05/062890A3 describe methods and systems for modulating electronic behavior of cardiac cells by genetic modification of inwardly rectifying $K^+$ channels ($I_{K1}$) in quiescent ventricular cells.

Another recent biological approach for moderating cardiac pacing involves implanting into the SA node or other suitable heart regions cells having particular ion channels that are commonly referred to as hyperpolarization-activated and cyclic nucleotide-gated (HCN) channels. For example, see PCT Publication Nos. WO 02/098286 and WO 05/062958A2. Physiologically originating in the SA node, the HCN channels play a prominent role in the control of rhythmic electrical heart activity. Cyclic nucleotides modulate the HCN channel activity, and channel activation occurs upon hyperpolarization rather than depolarization. There are four isoforms of HCN channels (HCN1-4), and each has greater or lesser prevalence in different heart regions. Because the HCN isoforms are directly involved in pacemaker current modulation and activation, implantation of HCN-expressing cells into cardiac tissue that is diseased or experiencing conduction blockage is a viable method for regulating cardiac pacemaker function.

In some situations, implanted wild type HCN isoforms may not produce or regulate sufficiently fast pacing stimuli. A need therefore exists for a biological composition or system that will ensure successful curative therapy for cardiac dysfunction. There is also a need for a method to implement such biological compositions or systems and thereby moderate cardiac pacemaker function.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

A composition is provided for implantation into cardiac tissue. The composition includes a biological pacemaker that, when implanted, expresses an effective amount of a mutated hyperpolarization-activated and cyclic nucleotide-gated (HCN) isoform to modify $I_h$ when compared with wild-type HCN.

Methods are also provided for implementing each of the biological pacemakers. The method includes implanting each of biological pacemakers into cardiac tissue.

Figure 1:
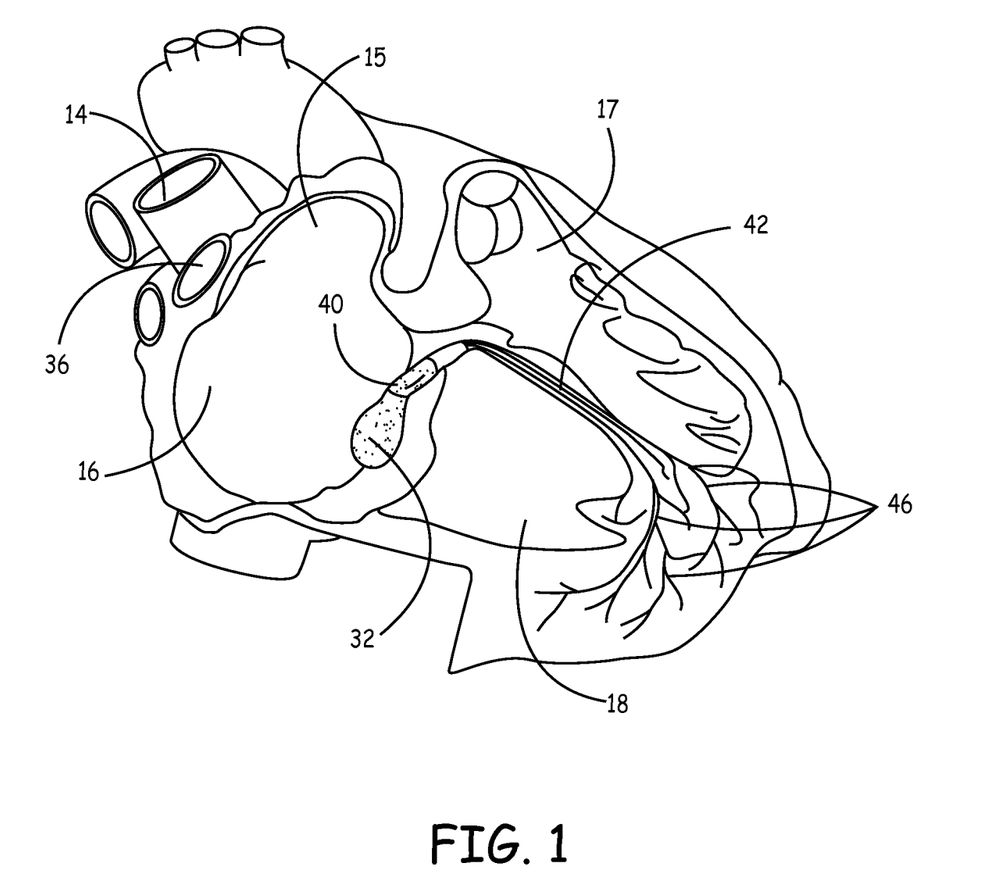
FIG. 1 is side view depicting the right side of a heart having an anterior-lateral wall peeled back to present a portion of a heart's intrinsic conduction system and chambers of a right atrium and a right ventricle.

FIG. 1 is side view of the right side of a heart having an anterior-lateral wall peeled back to present a portion of a heart's intrinsic conduction system and chambers of a right atrium 16 and a right ventricle 18. Pertinent elements of the heart's intrinsic conduction system include the SA node 36, the AV node 32, the bundle of His 40, the right bundle branch 42, and the Purkinje fibers 46. The left bundle branch is not depicted. The SA node 36 is shown at a junction between a superior vena cava 14 and the right atrium 16. An electric impulse initiated at the SA node 36 travels rapidly through the right atrium 16 and the non-illustrated left atrium to the AV node 32. At the AV node 32, the impulse slows to create a delay before passing on through the bundle of His 40, which branches, in an interventricular septum 17, into the right bundle branch 42 and the non-illustrated left bundle branch and then into the Purkinje fibers 46. The impulse then travels rapidly throughout the right ventricle 18 and the non-illustrated left ventricle. This electric impulse flow creates an orderly sequence of atrial and ventricular contraction to efficiently pump blood through the heart. If a portion of the heart's intrinsic conduction system becomes dysfunctional, efficient pumping is compromised.

A patient whose SA node 36 has become dysfunctional may undergo a pacemaker system implantation, which often includes placing lead electrodes in the right atrial appendage 15. The lead electrode stimulates the right atrium 16 downstream of the dysfunctional SA node 36, and the stimulating pulse travels on to the AV node 32, the bundle of His 40, and the Purkinje fibers 46 to restore physiological contraction of the heart at a regular and physiological rate.

Figure 2:
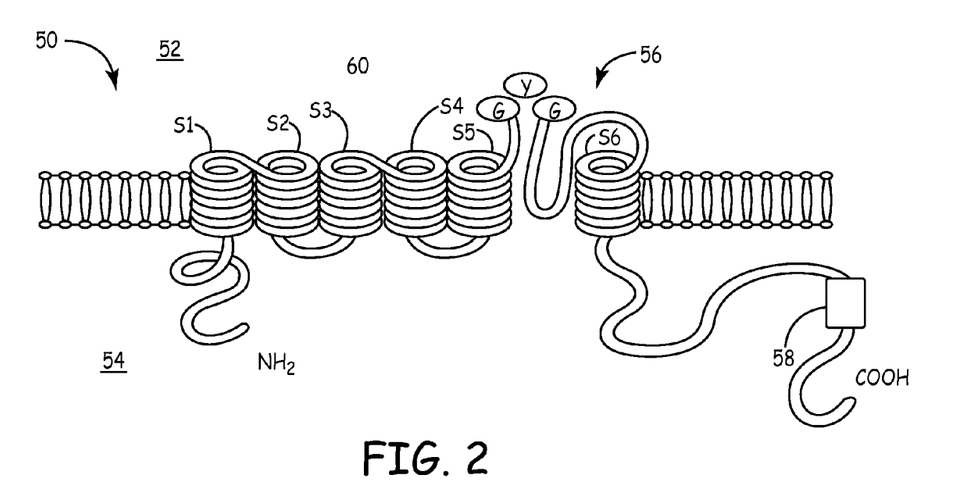
FIG. 2 is a cross-sectional view depicting a cardiac cell membrane including a mutated HCN-4 isoform as a HCN channel subunit according to an embodiment of the present invention.
Figure 3:
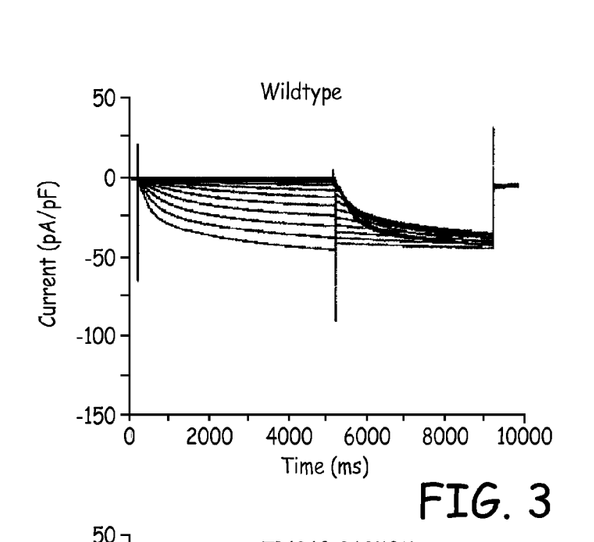
FIG. 3 is a graph depicting superimposed current traces of $I_h$ recorded from individual HEK293 cells transfected with the wild-type HCN-4 isoform.
Figure 4:
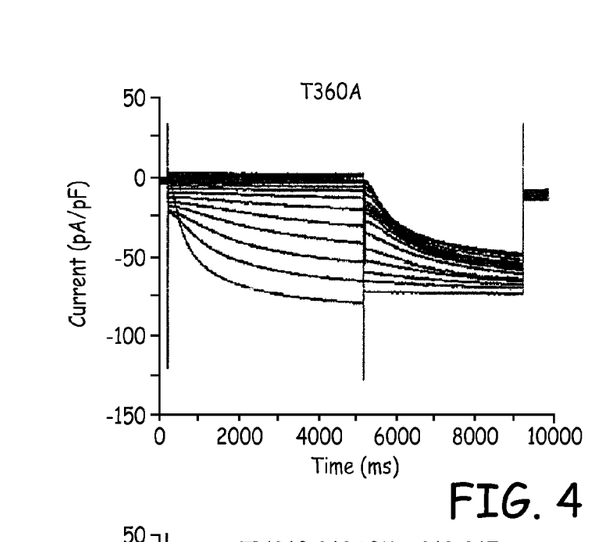
FIG. 4 is a graph depicting superimposed current traces of $I_h$ recorded from HEK293 cells transfected with the HCN-4 isoform including a T360A mutation according to an embodiment of the present invention.
Figure 5:
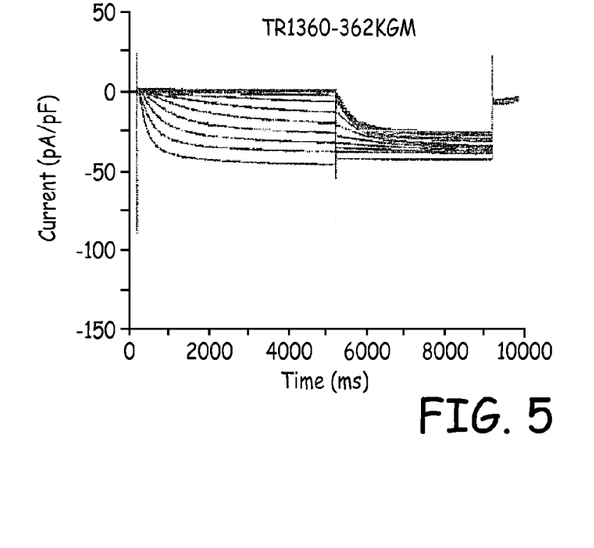
FIG. 5 is a graph depicting superimposed current traces of $I_h$ recorded from HEK293 cells transfected with the HCN-4 isoform including a TRI360-362KGM mutation according to an embodiment of the present invention.
Figure 6:
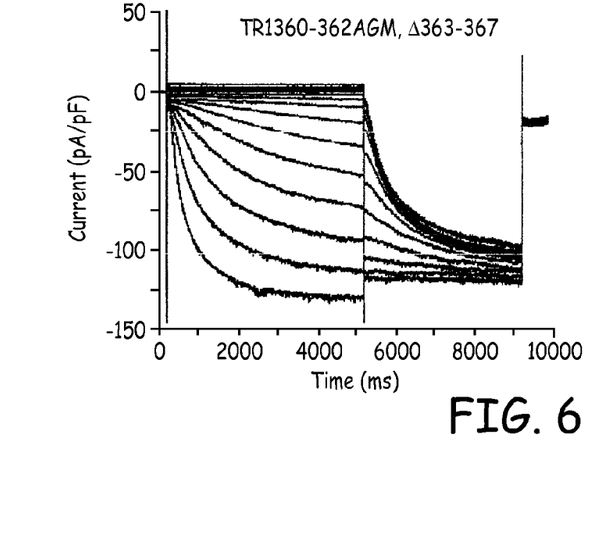
FIG. 6 is a graph depicting superimposed current traces of $I_h$ recorded from HEK293 cells transfected with the HCN-4 isoform including a TRI360-362AGM, Δ363-367 mutation according to an embodiment of the present invention.

As previously discussed, HCN channels play a prominent role in the control of rhythmic electrical activity of the heart. The HCN channels originate in the SA node and mediate hyperpolarization-activated cation ($Na^+$ and $K^+$) flows, commonly referred to as pacemaker currents and originally termed $I_f$ for "funny" in the heart and $I_h$ for "hyperpolarization" or $I_q$ for "queer" in neurons. The role of HCN channels in the generation of spontaneous activity and autonomic modulation of the heart has been demonstrated in several reports including Brown et al., *Nature* 280:235-36 (1979), DiFrancesco, *J. Physiol.* 314:359-76 (1981), DiFrancesco et al., *Nature* 351:145-7 (1991), and DiFrancesco, *Ann. Rev. Physiol.* 55:455-72 (1993). FIG. 2 is a cross-sectional view of a portion of a cardiac cell membrane 50 including a HCN channel subunit. More particularly, the depicted subunit is a HCN-4 isoform. HCN-4 is the most predominant HCN isoform in the SA node, accounting for a great majority of the total HCN mRNA in humans and other mammals. As with the other HCN isoforms (HCN1-3), the HCN-4 isoform has six transmembrane domains S1 to S6, and a cyclic nucleotide-binding domain (CNBD) 58. Both the $NH_2$ and COOH ends are in the intracellular region 54. A pore 56 is established between the S5 and S6 transmembrane domains, and a linker region in the extracellular region 52 between the S5 and S6 domains includes a GYG motif, which is a moderator of ion permeation.

One of many recent goals behind the development of biological pacemakers is increasing local expression of pacemaker currents in the heart. Therefore, recent research has been directed toward overexpression of HCN channels for the treatment of cardiac arrhythmia. Some recent studies demonstrate that overexpression of $I_h$ in myocytes via mouse HCN2 delivery, or implantation of stem cells with overexpression of mouse HCN-2, successfully induced automaticity of a biological pacemaker in arrhythmic animal models (see Qu et al., *Circulation* 107(8):1106-9 (2003); Plotnikov et al., *Circulation* 109(4):506-12 (2004); Potapova et al., *Circ. Res.* 94(7): 952-9 (2004); and Rosen et al., *Anat. Rec.* 280A(2):1046-52 (2004)). However, activation of HCN-4 may be slow or unreliable at physiological membrane potentials, which limits the ability for cells overexpressing HCN-4 to be used as a biological pacemaker. Moreover, HCN-4 is likely the most suitable isoform for creation of a biological pacemaker for numerous reasons. Firstly, HCN-4 is identical to the physiological isoform in the SA node. Furthermore, HCN-4 produces larger $I_f$ currents than other isoforms. HCN-4 is also, together with HCN2, the isoform most responsive to cAMP (by shifting $V_{1/2}$, and shifting activation kinetics), hence allowing for superior modulation of heart rates via either increased cAMP levels during sympathetic stimulation (e.g. stress, exercise), or decreased cAMP levels (e.g. sleep, rest). See Biel et al. *Trends Cardiovasc. Med.* 12(5):206-12 (2002).

In view of the slow or unreliable activation for wild type HCN in cardiac tissue, one aspect of the present invention is to produce and implant into cardiac tissue one or more biological pacemakers. As used herein, the term "biological pacemaker" refers to a polynucleotide composition, or a cell-based composition having a specific modified polynucleotide composition for modulating cardiac contraction to desired levels.

Polynucleotides of choice can be made by traditional PCR-based amplification and known cloning techniques. Alternatively, a polynucleotide of the invention can be made by automated procedures that are well known in the art. A polynucleotide of the invention should include a start codon to initiate transcription and a stop codon to terminate translation. Suitable polynucleotides for use with the invention can be obtained from a variety of public sources including, without limitation, GenBank (National Center for Biotechnology Information (NCBI)), EMBL data library, SWISS-PROT (University of Geneva, Switzerland), the PIR-International database; and the American Type Culture Collection (ATCC) (10801 University Boulevard, Manassas, Va. 20110-2209). See generally, Benson, D. A. et al, *Nucl. Acids. Res.*, 25:1 (1997) for a description of GenBank. The particular polynucleotides useful with the present invention are readily obtained by accessing public information from GenBank.

Any suitable DNA vector or delivery vehicle may be utilized to transfer the desired nucleotide sequence to the targeted cardiac cells. For example, the nucleotide sequence may be cloned into a viral vector such as an adenoviral associated vector (AAV) or other viral vectors such as herpes vectors, and retroviral vectors such as lentiviral vectors. The type of viral vector selected is dependent on the target tissue and the length of the sequence to be delivered. For a discussion of viral vectors see *Gene Transfer and Expression Protocols*, Murray ed., pp. 109-206 (1991). Alternatively, non-viral delivery systems may be utilized. For example, liposome:DNA complexes, plasmid:liposome complexes, naked DNA, DNA-coated particles, or polymer based systems may be used to deliver the desired sequence to the targeted cardiac cells. The above-mentioned delivery systems and protocols therefore are described in *Gene Targeting Protocols*, Kmeic 2ed. pp. 1-35 (2002), and *Gene Transfer and Expression Protocols*, Vol. 7, Murray ed. pp 81-89 (1991).

AAV vectors can be constructed using techniques well known in the art. Typically, the vector is constructed so as to provide operatively linked components of control elements.

For example, a typical vector includes a transcriptional initiation region, a nucleotide sequence of the protein to be expressed, and a transcriptional termination region. Typically, such an operatively linked construct will be flanked at its 5' and 3' regions with AAV ITR sequences, which are required viral cis elements. The control sequences can often be provided from promoters derived from viruses such as, polyoma, Adenovirus 2, cytomegalovirus, and Simian Virus 40. Viral regulatory sequences can be selected to achieve a high level of expression in a variety of cells. Alternatively, ubiquitously expressing promoters, such as the early cytomegalovirus promoter can be utilized to accomplish expression in any cell type. A third alternative is the use of promoters that drive tissue specific expression. This approach is particularly useful where expression of the desired protein in non-target tissue may have deleterious effects. Thus, according to another preferred embodiment, the vector contains the proximal human brain natriuretic brain (hBNP) promoter that functions as a cardiac-specific promoter. For details on construction of such a vector see LaPointe et al., *Left Ventricular Targeting of Reporter Gene Expression In Vivo by Human BNP Promoter in an Adenoviral Vector*, Am. J. Physiol. Heart Circ. Physiol., 283:H1439-45 (2002).

Vectors may also contain cardiac enhancers to increase the expression of the transgene in the targeted regions of the cardiac conduction system. Such enhancer elements may include the cardiac specific enhancer elements derived from Csx/Nkx2.5 regulatory regions disclosed in the published U.S. Patent Application 20020022259, the teachings of which are herein incorporated by reference.

Therapeutic methods of the present invention include delivery of an effective amount of a genetic construct or genetically engineered cells or unmodified cells with pacemaking activity to the cardiac cells to produce a biological pacemaker that increases the intrinsic pacing rate of such cells. The biological pacemakers may be introduced using genetically engineered vectors, genetically engineered cells, or unmodified cells, which are implanted at a selected location. One delivery method includes the use of a delivery tool, such as a catheter having electric sensing capabilities, which is introduced directly into either the targeted cardiac tissue. The delivery tool may include electrodes for sensing electric activity and delivering pacing stimuli in order to determine the desired location for the biological pacemakers. Once the location is determined, genetically engineered viruses, gene-modified cells or unmodified cells are delivered to the myocardium at that location to form a biological pacemaker. The delivery tool may include an injection device that injects the viruses or cells into the myocardium. One suitable method for injecting a genetic construct directly into the myocardium is described by R. J. Guzman et al., *Circ. Res.*, 73:1202-1207 (1993). Furthermore, a delivery system for delivering genetic material to a targeted heart region is described in U.S. Pat. No. 7,103,418 and PCT Publication No. WO 98/02150, the teachings of which are incorporated herein by reference. Alternatively, genetically engineered cells may be cultured and proliferated on a solid scaffold, and then surgically delivered to the selected heart region together with the scaffold. The scaffold may also be directly injected into the myocardium.

Perfusion protocols that are useful with the inventive methods are often sufficiently capable of delivering a genetic construct to at least about 10% of cardiac myocytes. Infusion volumes of between about 0.01 ml and about 1 ml are useful for direct intramyocardial injection. Also, suitable methods for targeting non-viral vector genetic constructs to the heart are described in U.S. Pat. No. 6,376,471, the teachings of which are hereby incorporated by reference.

When a genetic construct (in contrast to genetically engineered cells) is introduced to the myocardium using any suitable technique, the genetic material is delivered into the cells by, for example, transfection or transduction procedures. Transfection and transduction refer to the acquisition by a cell of new genetic material by incorporation of added nucleic acid molecules. Transfection can occur by physical or chemical methods. Many transfection techniques are known to those of ordinary skill in the art including, without limitation, calcium phosphate DNA co-precipitation, DEAE-dextrin DNA transfection, electroporation, naked plasmid adsorption, and cationic liposome-mediated transfection (commonly known as lipofection). Transduction refers to the process of transferring nucleic acid into a cell using a DNA or RNA virus. Suitable viral vectors for use as transducing agents include, but are not limited to, retroviral vectors, adeno-associated viral vectors, lentiviral vectors, herpes simplex viral vectors, vaccinia viruses, and Semliki Foret virus vectors.

The biological pacemakers of the present invention include mutated HCN isoforms that accelerate activation and deactivation kinetics of the HCN channel that includes the mutated HCN subunit. One recent report, Tsang et al., *J Biol Chem.* 279(42):43752-9 (2004), discloses that mutations in the S3-S4 linker of HCN-1 subunits in HCN channels alter the kinetics of channel activation and deactivation. Some exemplary embodiments of the present invention include production and implantation of human HCN isoforms having a S3-S4 linker mutation, and of a HCN channel that includes the mutated HCN subunit, to thereby enable the channel to activate at desirable membrane potentials.

According to an exemplary embodiment, one or more biological pacemakers are implanted in, or downstream from in the conduction pathway, a heart region that is experiencing or may experience poor conduction. For example, if cardiac contraction is not being properly initiated by the SA node, the one or more biological pacemakers may be implanted in the myocardium of the SA node or the right atrium to cause the targeted region to depolarize and create electric impulses that will travel to the AV node. Alternatively, if cardiac contraction is not being properly initiated by the SA node then the backup biological pacemakers may be implanted downstream in the conduction pathway from the right atrium, i.e. in the bundle of His, the Purkinje network, or one of the ventricles.

Returning to FIG. 2, the HCN-4 subunit included in the cardiac cell membrane 50 has a mutated S3-S4 linker 60. The wild type amino acid sequence (SEQ. ID. 1) for HCN-4 is listed below. The sequence for the S3-S4 linker is underlined, and spans residues 359-367.

```
SEQ. ID 1:
  1    MDKLPPSMRK  RLYSLPQQVG  AKAWIMDEEE  DAEEEGAGGR

41    QDPSRRSIRL  RPLPSPSPSA  AAGGTESRSS  ALGAADSEGP

81    ARGAGKSSTN  GDCRRFRGSL  ASLGSRGGGS  GGTGSGSSHG

121    HLHDSAEERR  LIAEGDASPG  EDRTPPGLAA  EPERPGASAQ

161    PAASPPPPQQ  PPQPASASCE  QPSVDTAIKV  EGGAAAGDQI

201    LPEAEVRLGQ  AGFMQRQFGA  MLQPGVNKFS  LRMFGSQKAV

241    EREQERVKSA  GFWIIHPYSD  FRFYWDLTML  LLMVGNLIII

281    PVGITFFKDE  NTTPWIVFNV  VSDTFFLIDL  VLNFRTGIVV

321    EDNTEIILDP  QRIKMKYLKS  WFMVDFISSI  PVDYIFLIVE
```

```
 361  TRIDSEVYKT ARALRIVRFT KILSLLRLLR LSRLIRYIHQ

401  WEEIFHMTYD LASAVVRIVN LIGMMLLLCH WDGCLQFLVP

441  MLQDFPDDCW VSINNMVNNS WGKQYSYALF KAMSHMLCIG

481  YGRQAPVGMS DVWLTMLSMI VGATCYAMFI GHATALIQSL

521  DSSRRQYQEK YKQVEQYMSF HKLPPDTRQR IHDYYEHRYQ

561  GKMFDEESIL GELSEPLREE IINFNCRKLV ASMPLFANAD

601  PNFVTSMLTK LRFEVFQPGD YIIREGTIGK KMYFIQHGVV

641  SVLTKGNKET KLADGSYFGE ICLLTRGRRT ASVRADTYCR

681  LYSLSVDNFN EVLEEYPMMR RAFETVALDR LDRIGKKNSI

721  LLHKVQHDLN SGVFNYQENE IIQQIVQHDR EMAHCAHRVQ

761  AAASATPTPT PVIWTPLIQA PLQAAAATTS VAIALTHHPR

801  LPAAIFRPPP GSGLGNLGAG QTPRHLKRLQ SLIPSALGSA

841  SPASSPSQVD TPSSSSFHIQ QLAGFSAPAG LSPLLPSSSS

881  SPPPGACGSP SAPTPSAGVA ATTIAGFGHF HKALGGSLSS

921  SDSPLLTPLQ PGARSPQAAQ PSPAPPGARG GLGLPEHFLP

961  PPPSSRSPSS SPGQLGQPPG ELSLGLATGP LSTPETPPRQ

1001  PEPPSLVAGA SGGASPVGFT PRGGLSPPGH SPGPPRTFPS

1041  APPRASGSHG SLLLPPASSP PPPQVPQRRG TPPLTPGRLT

1081  QDLKLISASQ PALPQDGAQT LRRASPHSSG ESMAAFPLFP

1121  RAGGGSGGSG SSGGLGPPGR PYGAIPGQHV TLPRKTSSGS

1161  LPPPLSLFGA RATSSGGPPL TAGPQREPGA RPEPVRSKLP

1201  SNL
```

According to some exemplary embodiments of the invention, the S3-S4 linker in the HCN-4 isoform is mutated to have a sequence selected from those listed in Table 1 below. Unless otherwise noted, for each of the listed mutations the remaining sequence is identical to that of the wild-type HCN-4. Also, in other exemplary embodiments mutations are made within the S4 segment. These and other similar mutations may also be made to the S3-S4 linker for other HCN isoforms (HCN 1-3). The mutations are tailored to change the HCN channel activity with respect to the pacemaker current $I_h$. Some mutations are tailored to increase the activation kinetics for the HCN channel. Other mutations are tailored to increase the deactivation kinetics or the $V_{1/2}$ activation for the HCN channel.

TABLE 1

| SEQ. ID # | Mutant | S3-4 Linker (359-367) |
|---|---|---|
| 2 | Wild-type HCN4 | ETRIDSEVY |
| 3 | T360A | EARIDSEVY |
| 4 | Δ363-367 | ETRI |
| 5 | T360A, Δ363-367 | EARI |
| 6 | TRI360-362AGM | EAGMDSEVY |
| 7 | TRI360-362KGM | EKGMDSEVY |
| 8 | T360A, I362M | EARMDSEVY |
| 9 | T360A, Δ365-367 | EARIDS |
| 10 | E365G | ETRIDSGVY |
| 11 | E365A | ETRIDSAVY |
| 12 | R361G | ETGIDSEVY |
| 13 | TR360-361AA | EAAIDSEVY |
| 14 | I362C | ETRCDSEVY |
| 15 | I362S | ETRSDSEVY |
| 16 | I362T | ETRTDSEVY |
| 17 | TRI360-362AGM, Δ363-367 | EAGM |

According to other embodiments, the HCN-4 isoform includes one of the mutations listed in Table 1, and some of the C-terminal region of the amino acid sequence is truncated. For some particular embodiments, the C-terminal region is truncated after 16 amino acid residues from the CNBD toward the C-terminal (i.e. by deleting (Δ) nucleotides 2261-3612 from the 3612 nucleotide coding sequence). The coding sequence for wild type HCN-4 is listed below (SEQ. ID 18), with nucleotides underlined to illustrate the region that is deleted according to particular embodiments. These truncations have been described in WO05062958A2, which is incorporated herein by reference.

```
SEQ. ID 18:
   1 atggacaagc tgccgccgtc catgcgcaag cggctctaca gcctcccgca gcaggtgggg 61 gccaaggcgt ggatcatgga cgaggaagag gacgccgagg aggaggggc cgggggccgc 121 caagacccca gccgcaggag catccggctg cggccactgc cctcgccctc ccctcggcg 181 gccgcgggtg gcacggagtc ccggagctcg gccctcgggg cagcggacag cgaagggccg 241 gcccgcggcg cgggcaagtc cagcacgaac ggcgactgca ggcgcttccg cgggagcctg 301 gcctcgctgg gcagccgggg cggcggcagc ggcggcacgg ggagcggcag cagtcacgga 361 cacctgcatg actccgcgga ggagcggcgg ctcatcgccg agggcgacgc gtccccggc 421 gaggacagga cgccccagg cctggcgcc gagcccgagc gccccggcgc ctcggcgcag
```

-continued

```
 481 cccgcagcct cgccgccgcc gccccagcag ccaccgcagc cggcctccgc ctcctgcgag 541 cagccctcgg tggacaccgc tatcaaagtg gagggaggcg cggctgccgg cgaccagatc 601 ctcccggagg ccgaggtgcg cctgggccag gccggcttca tgcagcgcca gttcggggcc 661 atgctccaac ccggggtcaa caaattctcc ctaaggatgt tcggcagcca gaaagccgtg 721 gagcgcgaac aggagagggt caagtcggcc ggattttgga ttatccaccc ctacagtgac 781 ttcagatttt actgggacct gaccatgctg ctgctgatgg tgggaaacct gattatcatt 841 cctgtgggca tcaccttctt caaggatgag aacaccacac cctggattgt cttcaatgtg 901 gtgtcagaca cattcttcct catcgacttg gtcctcaact tccgcacagg gatcgtggtg 961 gaggacaaca cagagatcat cctggacccg cagcggatta aaatgaagta cctgaaaagc 1021 tggttcatgg tagatttcat ttcctccatc cccgtggact acatcttcct cattgtggag 1081 acacgcatcg actcggaggt ctacaagact gcccgggccc tgcgcattgt ccgcttcacg 1141 aagatcctca gcctcttacg cctgttacgc ctctcccgcc tcattcgata tattcaccag 1201 tgggaagaga tcttccacat gacctacgac ctggccagcg ccgtggtgcg catcgtgaac 1261 ctcatcggca tgatgctcct gctctgccac tgggacggct gcctgcagtt cctggtaccc 1321 atgctacagg acttccctga cgactgctgg gtgtccatca caacatggt gaacaactcc 1381 tgggggaagc agtactccta cgcgctcttc aaggccatga ccacatgct gtgcatcggc 1441 tacgggcggc aggcgcccgt gggcatgtcc gacgtctggc tcaccatgct cagcatgatc 1501 gtgggtgcca cctgctacgc catgttcatt ggccacgcca ctgccctcat ccagtccctg 1561 gactcctccc ggcgccagta ccaggaaaag tacaagcagg tggagcagta catgtccttt 1621 cacaagctcc cgcccgacac ccggcagcgc atccacgact actacgagca ccgctaccag 1681 ggcaagatgt cgacgagga gagcatcctg gcgagctaa gcgagcccct gcgggaggag 1741 atcatcaact ttaactgtcg gaagctggtg gcctccatgc cactgtttgc caatgcggac 1801 cccaacttcg tgacgtccat gctgaccaag ctgcgtttcg aggtcttcca gcctggggac 1861 tacatcatcc gggaaggcac cattggcaag aagatgtact tcatccagca tggcgtggtc 1921 agcgtgctca ccaagggcaa caaggagacc aagctggccg acggtcccta ctttggagag 1981 atctgcctgc tgacccgggg ccggcgcaca gccagcgtga gggccgacac ctactgccgc 2041 ctctactcgc tgagcgtgga caacttcaat gaggtgctgg aggagtaccc catgatgcga 2101 agggccttcg agaccgtggc gctggaccgc ctggaccgca ttggcaagaa gaactccatc 2161 ctcctccaca aagtccagca cgacctcaac tccggcgtct tcaactacca ggagaatgag 2221 atcatccagc agattgtgca gcatgaccgg gagatggccc actgcgcgca ccgcgtccag 2281 gctgctgcct ctgccacccc aaccccacg cccgtcatct ggaccccgct gatccaggca 2341 ccactgcagg ctgccgctgc caccacttct gtggccatag ccctcaccca ccaccctcgc 2401 ctgcctgctg ccatcttccg ccctccccca ggatctgggc tgggcaacct cggtgccggg 2461 cagacgccaa ggcacctgaa acggctgcag tccctgatcc cttctgcgct gggctccgcc 2521 tcgcccgcca gcagcccgtc ccaggtggac acaccgtctt catcctcctt ccacatccaa 2581 cagctggctg gattctctgc cccgctgga ctgagcccac tcctgccctc atccagctcc 2641 tccccacccc ccgggcctg tggctccccc tcggctccca ccatcagc tggcgtagcc 2701 gccaccacca tagccgggtt tggccacttc cacaaggcgc tgggtggctc cctgtcctcc 2761 tccgactctc ccctgctcac cccgctgcag ccaggcgccc gctcccgca ggctgcccag 2821 ccatctcccg cgcacccgg ggcccgggga ggctgggac tccggagca cttcctgcca 2881 ccccacccct catccagatc cccgtcatct agccccgggc agctgggcca gcctcccggg
```

-continued

```
2941 gagttgtccc taggtctggc cactggccca ctgagcacgc cagagacacc cccacggcag 3001 cctgagccgc cgtcccttgt ggcagggggcc tctgggggggg cttccctgt aggctttact 3061 ccccgaggag gtctcagccc ccctggccac agcccaggcc ccccaagaac cttcccgagt 3121 gccccgcccc gggcctctgg ctcccacgga tccttgctcc tgccacctgc atccagcccc 3181 ccaccacccc aggtccccca gcgccggggc acacccccgc tcaccccgg ccgcctcacc 3241 caggacctca agctcatctc cgcgtctcag ccagccctgc ctcaggacgg ggcgcagact 3301 ctccgcagag cctccccgca ctcctcaggg gagtccatgg ctgccttccc gctcttcccc 3361 agggctgggg gtggcagcgg gggcagtggg agcagcgggg gcctcggtcc ccctgggagg 3421 ccctatggtg ccatccccgg ccagcacgtc actctgcctc ggaagacatc ctcaggttct 3481 ttgccacccc ctctgtcttt gtttggggca agagccacct cttctggggg gccccctctg 3541 actgctggac cccagaggga acctggggcc aggcctgagc cagtgcgctc caaactgcca 3601 tccaatctat ga
```

It follows that additional exemplary embodiments include a HCN-4 channel including the isoform having the sequence of SEQ. ID. 18, with either mutation T360A, mutation TRI360-362KGM or TRI360-362AGM, Δ363-367, along with truncation of HCN-4 after the CNBD. Any of such plasmids may be cloned into an adeno-associated virus (AAV) vector such as the AAV 2/9 vector, with either a cardiac specific promoter or constitutive promoters such as CMV or CAG. Such constructs are suitable for a biological pacemaker application, as AAV 2/9 has been demonstrated to have high specificity to cardiac tissue, and high efficiency in cardiac transduction (see Circ. Res. 18; 99(4):e3-9 (2006). The truncation of the C-terminus would allow packaging of HCN-4 mutations T360A, TRI360-362KGM, or TRI360-362AGM, Δ363-367 into the MV 2/9 expression cassette. MV 2/9 means that the vector contains a rep protein derived from MV 2, and a cap (capsid) protein from MV 9 serotype.

Example

Wild-type HCN-4 and S3-S4 linker mutants were tranfected into 50% confluent human embryonic kidney (HEK293) cells using known transfection reagents and standard methods. The selected S3-S4 linker mutants were T360A, TRI360-362KGM, and TRI360-362AGM, Δ363-367, the amino acid sequences for each being listed in Table 1. After transfection was completed, the cells were replated and cultured. The electrophysiologic properties of each mutant were examined using the so-called "whole-cell patch-clamp technique," which is described in Hamill et al., *Pflugers Arch.* 391 (2):85-100 (1981).

For the cells expressing the wild-type HCN-4, and also for the cells expressing the S3-S4 linker mutants, the hyperpolarization-activated cyclic nucleotide-gated inward current ($I_h$) was evoked by 5 s hyperpolarizing steps to potentials ranging from 0 to −140 mV, with a holding potential set at −40 mV. The reversal potential of $I_h$ was evaluated by tail currents recorded by 3 s 'tail' steps to membrane potentials ranging from −80 to 20 mV in 10 mV increments followed a 5 s conditioning potential step to −130 mV every 15 s, with the holding potential set at −40 mV. The activation of $I_h$ was elicited by 3 s 'tail' pulses to −130 mV followed by 5 s conditioning pulses from 0 mV to −140 mV in 10 mV increments, with the membrane holding potential set at −40 mV and a pulse rate of every 30 s. $I_h$ was evaluated at a point near the end of each test pulse. The current amplitudes were normalized with respect to corresponding membrane capacitance ($C_m$) values to minimize current differences due to cell size. A single-exponential fit of current traces allowed derivation of time constants for current activation and deactivation. Some data were fitted by a Boltzmann equation $\{1/[1+\exp(V_{1/2}-V)/k]$, where $V_{1/2}$ is the half-inactivation potential, V is the voltage potential, and k is the slope factor (in mV/e-fold change in current)}. The best-fit procedure was performed with a commercial software program (Origin 7.0, Microcal™ Software Inc.).

Figure 7:
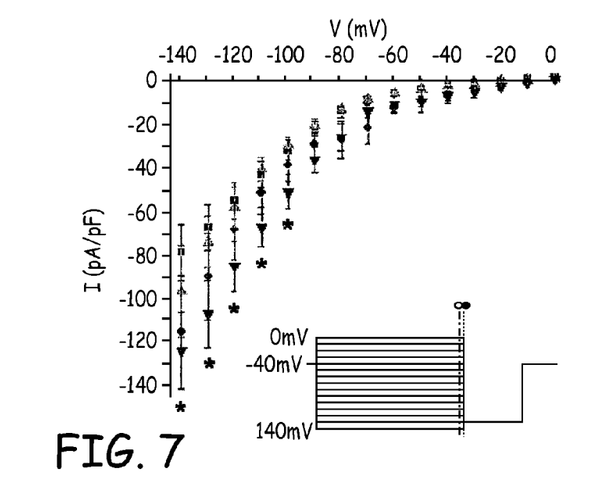
FIG. 7 is a graph depicting a current-voltage relationship for HEK293 cells transfected with wild-type and mutated HCN-4 isoforms, and an inset graph depicting a voltage-clamp protocol used for activation of $I_h$.
Figure 8:
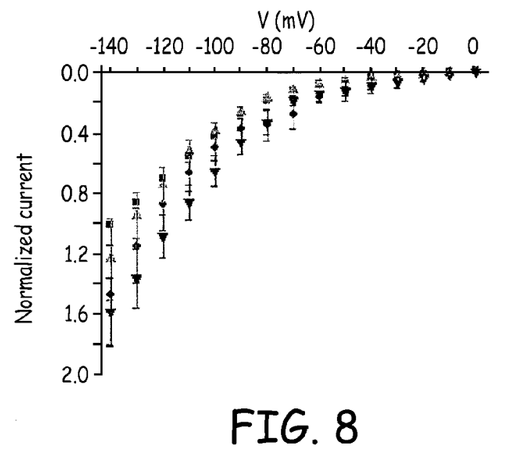
FIG. 8 is a graph depicting a current-voltage relationship for HEK293 cells transfected with wild-type and mutated HCN-4 isoforms, with the data normalized by the maximal current density of the cells transfected with the HCN-4 wild-type isoform.
Figure 9:
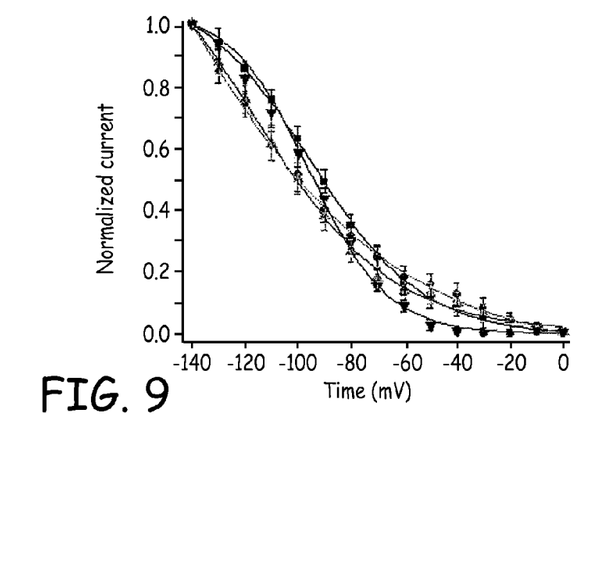
FIG. 9 is a graph depicting normalized activation conductances of $I_h$ for HEK293 cells transfected with wild-type and mutated HCN-4 isoforms.
Figure 10:
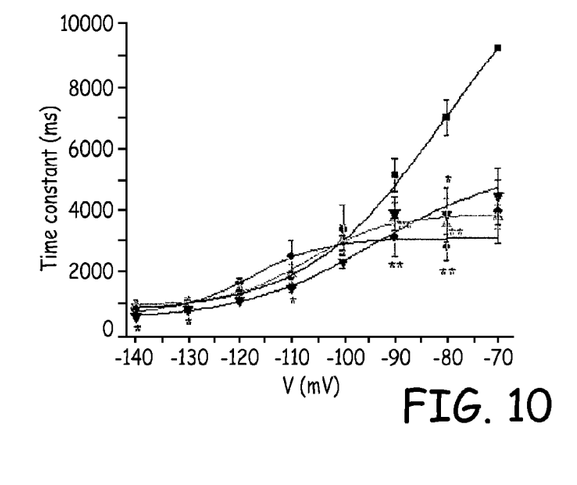
FIG. 10 is a graph depicting activation time constants of $I_h$ at different pulse voltages for HEK293 cells transfected with wild-type and mutated HCN-4 isoforms.

FIGS. 3 to 6 are graphs including superimposed current traces of $I_h$ for the cells transfected with either the HCN-4 wild-type isoform or with one of the three mutants. As seen from the graphs, the cells transfected with the T360A or the TRI360-362AGM, Δ363-367 mutation had more currents at particular negative voltages than the cells transfected with the HCN-4 wild-type isoform. FIG. 7 is a graph of the current-voltage relationship that was plotted according to the current density (pA/pF) of each test pulse. The inset graph in FIG. 7 depicts the voltage-clamp protocol used for activation of $I_h$. To measure the current-voltage relationship, each test pulse was measured at the end of the 5-s pulse, particularly at the first vertical dotted line (○) from the inset graph. For each of FIGS. 7 to 10, the trace designated with the ■ marker corresponds to the cells transfected with the HCN-4 wild-type isoform, the trace designated with the ♦ marker corresponds to the cells transfected with the HCN-4 isoform with the T360A mutation, the trace with the ▲ marker corresponds to the cells transfected with the HCN-4 isoform with the TRI360-362KGM mutation, and the trace designated with the ▼ marker corresponds to the cells transfected with the HCN-4 isoform with the TRI360-362AGM, Δ363-367 mutation. FIG. 8 is a graph depicting the current-voltage relationship for each type of transfected cells, with the data normalized by the maximal current density of the cells transfected with the HCN-4 wild-type isoform. FIG. 9 is a graph depicting the normalized activation conductances of $I_h$ for each type of transfected cells. The activation conductance curves were obtained by plotting the normalized values measured at the second dotted vertical line (●) of tail currents from the inset graph in FIG. 7 against the conditioning voltages. FIG. 10 is a graph depicting the activation time constants of $I_h$ at different pulse voltages for each type of transfected cells.

Table 2 lists each of the mutants (T360A, TRI360-362KGM, and TRI360-362AGM, Δ363-367) that were transfected into the HEK293 cells, and the $I_h$ test results for each S3-S4 linker mutant. More particularly, Table 2 summarizes the current densities and activation kinetics for the wild type and mutant cells corresponding to the test pulses from −40 to −130 mV.

TABLE 2

| Mutant | Density (pA/pF) | $V_{1/2}$ | Activation Kinetics | Deactivation Kinetics |
|---|---|---|---|---|
| T360A | −90.4 ± 19.8 | Unchanged | Faster | Unchanged |
| TRI360-362KGM | −74.5 ± 11.9 | Unchanged | Faster | Unchanged |
| TRI360-362AGM, Δ363-367 | −107.6 ± 15.5 | Unchanged | Faster | Unchanged |

Compared to the HCN-4 wildtype, there were some shifts of the activation curves for each of the three mutants. None of the voltage values of $V_{1/2}$ activation for any of the three mutants was significantly different from that of the wild-type HCN-4, and deactivation kinetics were not significantly changed for any of the three mutants. Compared to the HCN-4 wildtype, activation of $I_h$ at several voltages for T360A, TRI360-362KGM, and TRI360-362AGM, Δ363-367 was significantly faster.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A composition for implantation into cardiac tissue, comprising a biological pacemaker comprising a polynucleotide sequence encoding a mutated hyperpolarization-activated and cyclic nucleotide-gated (HCN) isoform that, when implanted, expresses an effective amount of the mutated HCN isoform to modify $I_h$ activation kinetics, wherein the HCN isoform is HCN-4, the mutation comprises a S3-S4 linker mutation, and the mutated HCN-4 demonstrates increased $I_h$ activation kinetics compared to wild type HCN-4.

2. The composition according to claim 1, comprising genetically engineered cells comprising the polynucleotide sequence encoding the mutated HCN-4 isoform.

3. The composition according to claim 1, wherein the S3-S4 linker mutation is selected from the group consisting of T360A, Δ363-367, T360A+Δ363-367, TRI360-362AGM, TRI360-362KGM, T360A+I362M, T360A+Δ365-367, E365G, E365A, R361G, TR360-361AA, I362C, I362S, I362T, and TRI360-362AGM+Δ363-367.

4. The composition according to claim 1, wherein the polynucleotide sequence encoding the mutated HCN-4 isoform further comprises a delivery vector.

5. The composition according to claim 4, wherein the delivery vector is an adeno-associated virus (AAV) vector.

6. The composition according to claim 1, wherein the mutated HCN-4 isoform further comprises a C-terminal region truncation.

7. The composition according to claim 6, wherein the truncation begins 16 amino acid residues past the cyclic nucleotide-binding domain (CNBD).

8. The composition according to claim 6, wherein the truncated, mutated HCN-4 isoform comprises a cyclic nucleotide-binding domain (CNBD) and is truncated past the CNBD.

9. A method for modifying pacemaker current in cardiac tissue, comprising implanting into heart tissue of a subject in need a composition of claim 1.

10. A method for modifying pacemaker current in cardiac tissue, the method comprising implanting into heart tissue of a subject in need a composition according to claim 2.

11. The method according to claim 9, wherein the S3-S4 linker mutation is selected from the group consisting of T360A, Δ363-367, T360A+Δ363-367, TRI360-362AGM, TRI360-362KGM, T360A+I362M, T360A+Δ365-367, E365G, E365A, R361G, TR360-361AA, I362C, I362S, I362T, and TRI360-362AGM +Δ363-367.

12. The method according to claim 9, wherein the polynucleotide sequence encoding the mutated HCN-4 isoform further comprises a delivery vector.

13. The method according to claim 12, wherein the delivery vector comprises an adeno-associated virus (AAV) vector.

14. The method according to claim 9, wherein the mutated HCN-4 isoform further comprises a C-terminal region truncation.

15. The method according to claim 14, wherein the truncated HCN-4 isoform includes a cyclic nucleotide-binding domain (CNBD) and is truncated past the CNBD.

16. The method according to claim 15, wherein the HCN-4 is truncated 16 amino acid residues past the CNBD.

17. A composition for implantation into cardiac tissue, comprising a biologcal pacemaker comprising a polynucleotide sequence encoding a mutated hyperpolarization-activated and cyclic nucleotide-gated (HCN) isoform that, when implanted, expresses an effective amount of the mutated HCN isoform to modify $I_h$ activation kinetics, wherein the HCN isoform is HCN-4 and the mutation comprises a S3-S4 linker mutation and wherein the mutated HCN-4 demonstrates increased $I_h$ activation kinetics compared to wild type HCN-4 and demonstrates $V_{1/2}$ kinetics that are unchanged compared to wild type HCN-4.

18. The composition according to claim 17, wherein the mutated HCN-4 comprises a S3-S4 linker mutation selected from the group consisting of T360A, T360A+Δ363-367, TRI360-362KGM, and TRI360-362AGM+Δ363-367.

19. A method for modifying pacemaker current in cardiac tissue, comprising implanting into heart tissue of a subject in need a composition according to claim 17.

20. The composition of claim 17 wherein the mutated HCN-4 further demonstrates deactivation kinetics that are unchanged compared to wild type HCN-4.

21. A composition for implantation into cardiac tissue comprising a polynucleotide sequence encoding a mutated hyperpolarization-activated and cyclic nucleotide-gated-4 (HCN-4) isoform, wherein the mutated HCN-4 comprises a S3-S4 linker mutation selected from the group consisting of T360A, T360A+Δ363-367, TRI360-362KGM, and TRI360-362AGM+Δ363-367.

22. A method for modifying pacemaker current in cardiac tissue, comprising implanting into heart tissue of a subject in need a composition according to claim 21.

23. The composition according to claim 21, wherein the mutated HCN-4 comprises the S3-S4 linker mutation T360A+Δ363-367.

24. The composition according to claim 21, wherein the mutated HCN-4 isoform further comprises a C-terminal region truncation.

25. The composition according to claim 23, wherein the mutated HCN-4 isoform further comprises a C-terminal region truncation.

26. The composition according to claim 23, wherein the polynucleotide sequence encoding the mutated HCN-4 isoform further comprises a delivery vector.

27. An isolated polynucleotide sequence that encodes a mutated HCN-4 comprising a S3-S4 linker mutation selected from the group consisting of T360A, T360A+Δ363-367, TRI360-362KGM, and TRI360-362AGM +66 363-367.

28. The isolated polynucleotide sequence of claim 27, wherein the mutated HCN-4 further comprises a C-terminal region truncation.

29. A method for modifying pacemaker current in cardiac tissue, the method comprising implanting into heart tissue of a subject in need an isolated polynucleotide sequence of claim 27.

30. The isolated polynucleotide sequence of claim 27, wherein the isolated polynucleotide sequence further comprises a delivery vector.

31. The isolated polynucleotide sequence of claim 30, wherein the delivery vector comprises an adeno-associated virus (AAV) vector.

32. An isolated genetically engineered cell comprising the isolated polynucleotide sequence of claim 27.

33. The isolated polynucleotide sequence of claim 28, wherein the truncation begins 16 amino acid residues past the cyclic nucleotide-binding domain (CNBD).

34. The isolated polynucleotide sequence of claim 28, wherein the truncated, mutated HCN-4 comprises a cyclic nucleotide-binding domain (CNBD) and is truncated past the CNBD.

35. The isolated polynucleotide sequence of claim 28, wherein the isolated polynucleotide sequence further comprises a delivery vector.

36. The isolated polynucleotide sequence of claim 35, wherein the delivery vector comprises an adeno-associated virus (AAV) vector.

37. The isolated polynucleotide sequence of claim 33, wherein the isolated polynucleotide sequence further comprises a delivery vector.

38. The isolated polynucleotide sequence of claim 37, wherein the delivery vector comprises an adeno-associated virus (AAV) vector.

39. The isolated polynucleotide sequence of claim 34, wherein the isolated polynucleotide sequence further comprises a delivery vector.

40. The isolated polynucleotide sequence of claim 39, wherein the delivery vector comprises an adeno-associated virus (AAV) vector.

* * * * *

UNITED STATES PATENT AND TRADEMARK OFFICE
CERTIFICATE OF CORRECTION

| | | |
|---|---|---|
| PATENT NO. | : 8,076,305 B2 | Page 1 of 1 |
| APPLICATION NO. | : 11/565433 | |
| DATED | : December 13, 2011 | |
| INVENTOR(S) | : Daniel C. Sigg et al. | |

It is certified that error appears in the above-identified patent and that said Letters Patent is hereby corrected as shown below:

Col. 22, Line 42

Error reads as: "...TRI360-362AGM+66 363-367."

Correction to Patent Should be: "...TRI360-362AGM + $\Delta$363-367."

Signed and Sealed this
Thirty-first Day of July, 2012

David J. Kappos
*Director of the United States Patent and Trademark Office*

SEQUENCE LISTING

```
<160> NUMBER OF SEQ ID NOS: 3

<210> SEQ ID NO 1
<211> LENGTH: 711
<212> TYPE: DNA
<213> ORGANISM: Human
<220> FEATURE:
<221> NAME/KEY: misc_feature
<222> LOCATION: (6)..(6)
<223> OTHER INFORMATION: n is a, c, g, t or u
<220> FEATURE:
<221> NAME/KEY: misc_feature
<222> LOCATION: (12)..(12)
<223> OTHER INFORMATION: n is a, c, g, t or u
<220> FEATURE:
<221> NAME/KEY: misc_feature
<222> LOCATION: (19)..(19)
<223> OTHER INFORMATION: n is a, c, g, t or u
<220> FEATURE:
<221> NAME/KEY: misc_feature
<222> LOCATION: (81)..(81)
<223> OTHER INFORMATION: n is a, c, g, t or u
<220> FEATURE:
<221> NAME/KEY: misc_feature
<222> LOCATION: (165)..(165)
<223> OTHER INFORMATION: n is a, c, g, t or u
<220> FEATURE:
<221> NAME/KEY: misc_feature
<222> LOCATION: (195)..(195)
<223> OTHER INFORMATION: n is a, c, g, t or u
<220> FEATURE:
<221> NAME/KEY: misc_feature
<222> LOCATION: (200)..(200)
<223> OTHER INFORMATION: n is a, c, g, t or u
<220> FEATURE:
<221> NAME/KEY: misc_feature
<222> LOCATION: (203)..(203)
<223> OTHER INFORMATION: n is a, c, g, t or u
<220> FEATURE:
<221> NAME/KEY: misc_feature
<222> LOCATION: (210)..(210)
<223> OTHER INFORMATION: n is a, c, g, t or u
<220> FEATURE:
<221> NAME/KEY: misc_feature
<222> LOCATION: (216)..(216)
<223> OTHER INFORMATION: n is a, c, g, t or u
<220> FEATURE:
<221> NAME/KEY: misc_feature
<222> LOCATION: (268)..(268)
<223> OTHER INFORMATION: n is a, c, g, t or u
```

-continued

```
<220> FEATURE:
<221> NAME/KEY: misc_feature
<222> LOCATION: (287)..(288)
<223> OTHER INFORMATION: n is a, c, g, t or u
<220> FEATURE:
<221> NAME/KEY: misc_feature
<222> LOCATION: (291)..(292)
<223> OTHER INFORMATION: n is a, c, g, t or u
<220> FEATURE:
<221> NAME/KEY: misc_feature
<222> LOCATION: (368)..(369)
<223> OTHER INFORMATION: n is a, c, g, t or u
<220> FEATURE:
<221> NAME/KEY: misc_feature
<222> LOCATION: (378)..(378)
<223> OTHER INFORMATION: n is a, c, g, t or u
<220> FEATURE:
<221> NAME/KEY: misc_feature
<222> LOCATION: (381)..(381)
<223> OTHER INFORMATION: n is a, c, g, t or u
<220> FEATURE:
<221> NAME/KEY: misc_feature
<222> LOCATION: (406)..(406)
<223> OTHER INFORMATION: n is a, c, g, t or u
<220> FEATURE:
<221> NAME/KEY: misc_feature
<222> LOCATION: (434)..(435)
<223> OTHER INFORMATION: n is a, c, g, t or u
<220> FEATURE:
<221> NAME/KEY: misc_feature
<222> LOCATION: (452)..(452)
<223> OTHER INFORMATION: n is a, c, g, t or u
<220> FEATURE:
<221> NAME/KEY: misc_feature
<222> LOCATION: (459)..(459)
<223> OTHER INFORMATION: n is a, c, g, t or u
<220> FEATURE:
<221> NAME/KEY: misc_feature
<222> LOCATION: (463)..(463)
<223> OTHER INFORMATION: n is a, c, g, t or u
<220> FEATURE:
<221> NAME/KEY: misc_feature
<222> LOCATION: (465)..(465)
<223> OTHER INFORMATION: n is a, c, g, t or u
<220> FEATURE:
<221> NAME/KEY: misc_feature
<222> LOCATION: (504)..(504)
<223> OTHER INFORMATION: n is a, c, g, t or u
<220> FEATURE:
<221> NAME/KEY: misc_feature
<222> LOCATION: (711)..(711)
<223> OTHER INFORMATION: n is a, c, g, t or u
<400> SEQUENCE: 1
wdyamnacds uncsdrhcns dmdksmrkry svgakawmdd agaggrdsrr srrsssaaag 60
gsrssagaad sgargagkss ngdcrrrgsa sgsrgggsgg gsgsshghhd sarragdasg 120
drgaargasa aasasascsv dakvggaaag davrgagmrg amgvnksrmg skavrrvksa 180
gwhysdrywd mmvgnvgkdn wvnvvsddvn rgvvdndrkm kykswmvdss vdyvrdsvyk 240
ararvrksrr srryhwhmyd asavvrvngm mchwdgcvmd ddcwvsnnmv nnswgkysya 300
kamshmcgyg ravgmsdvwm smvgacyamg haasdssrry kykvymshkd rrhdyyhryg 360
kmdsgsrnnc rkvasmanad nvsmkrvgdy rggkkmyhgv vsvkgnkkad gsygcrgrra 420
svradycrys svdnnvymmr ravadrdrgk knshkvhdns gvnynvhdrm ahcahrvaaa 480
savwaaaaas vaahhraarg sggngagrhk rssagsasas ssvdssssha gsaagsssss 540
sgacgssasa gvaaagghhk aggssssdsg arsaasagar ggghssrsss sgggsgagsr 600
svagasggas vgrggsghsg rsarasgshg sassvrrggr dksasadgar rashssgsma 660
aragggsggs gssggggryg aghvrkssgs sgarassgga grgarvrsks n 711
```

```
<210> SEQ ID NO 2
<211> LENGTH: 711
<212> TYPE: RNA
<213> ORGANISM: Human
<220> FEATURE:
<221> NAME/KEY: misc_feature
<222> LOCATION: (6)..(6)
<223> OTHER INFORMATION: n is a, c, g, or u
<220> FEATURE:
<221> NAME/KEY: misc_feature
<222> LOCATION: (12)..(12)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u
<220> FEATURE:
<221> NAME/KEY: misc_feature
<222> LOCATION: (81)..(81)
<223> OTHER INFORMATION: n is a, c, g, or u
<220> FEATURE:
<221> NAME/KEY: misc_feature
<222> LOCATION: (165)..(165)
<223> OTHER INFORMATION: n is a, c, g, or u
<220> FEATURE:
<221> NAME/KEY: misc_feature
<222> LOCATION: (195)..(195)
<223> OTHER INFORMATION: n is a, c, g, or u
<220> FEATURE:
<221> NAME/KEY: misc_feature
<222> LOCATION: (200)..(200)
<223> OTHER INFORMATION: n is a, c, g, or u
<220> FEATURE:
<221> NAME/KEY: misc_feature
<222> LOCATION: (203)..(203)
<223> OTHER INFORMATION: n is a, c, g, or u
<220> FEATURE:
<221> NAME/KEY: misc_feature
<222> LOCATION: (210)..(210)
<223> OTHER INFORMATION: n is a, c, g, or u
<220> FEATURE:
<221> NAME/KEY: misc_feature
<222> LOCATION: (216)..(216)
<223> OTHER INFORMATION: n is a, c, g, or u
<220> FEATURE:
<221> NAME/KEY: misc_feature
<222> LOCATION: (268)..(268)
<223> OTHER INFORMATION: n is a, c, g, or u
<220> FEATURE:
<221> NAME/KEY: misc_feature
<222> LOCATION: (287)..(288)
<223> OTHER INFORMATION: n is a, c, g, or u
<220> FEATURE:
<221> NAME/KEY: misc_feature
<222> LOCATION: (291)..(292)
<223> OTHER INFORMATION: n is a, c, g, or u
<220> FEATURE:
<221> NAME/KEY: misc_feature
<222> LOCATION: (368)..(369)
<223> OTHER INFORMATION: n is a, c, g, or u
<220> FEATURE:
<221> NAME/KEY: misc_feature
<222> LOCATION: (378)..(378)
<223> OTHER INFORMATION: n is a, c, g, or u
<220> FEATURE:
<221> NAME/KEY: misc_feature
<222> LOCATION: (381)..(381)
<223> OTHER INFORMATION: n is a, c, g, or u
<220> FEATURE:
<221> NAME/KEY: misc_feature
<222> LOCATION: (406)..(406)
<223> OTHER INFORMATION: n is a, c, g, or u
<220> FEATURE:
<221> NAME/KEY: misc_feature
<222> LOCATION: (434)..(435)
<223> OTHER INFORMATION: n is a, c, g, or u
<220> FEATURE:
<221> NAME/KEY: misc_feature
<222> LOCATION: (452)..(452)
<223> OTHER INFORMATION: n is a, c, g, or u
```

-continued

```
<220> FEATURE:
<221> NAME/KEY: misc_feature
<222> LOCATION: (459)..(459)
<223> OTHER INFORMATION: n is a, c, g, or u
<220> FEATURE:
<221> NAME/KEY: misc_feature
<222> LOCATION: (463)..(463)
<223> OTHER INFORMATION: n is a, c, g, or u
<220> FEATURE:
<221> NAME/KEY: misc_feature
<222> LOCATION: (465)..(465)
<223> OTHER INFORMATION: n is a, c, g, or u
<220> FEATURE:
<221> NAME/KEY: misc_feature
<222> LOCATION: (504)..(504)
<223> OTHER INFORMATION: n is a, c, g, or u
<220> FEATURE:
<221> NAME/KEY: misc_feature
<222> LOCATION: (711)..(711)
<223> OTHER INFORMATION: n is a, c, g, or u
<400> SEQUENCE: 2
wdyamnacds uncsdrhcns dmdksmrkry svgakawmdd agaggrdsrr srrsssaaag     60
gsrssagaad sgargagkss ngdcrrrgsa sgsrgggsgg gsgsshghhd sarragdasg    120
drgaargasa aasasascsv dakvggaaag davrgagmrg amgvnksrmg skavrrvksa    180
gwhysdrywd mmvgnvgkdn wvnvvsddvn rgvvdndrkm kykswmvdss vdyvrdsvyk    240
ararvrksrr srryhwhmyd asavvrvngm mchwdgcvmd ddcwvsnnmv nnswgkysya    300
kamshmcgyg ravgmsdvwm smvgacyamg haasdssrry kykvymshkd rrhdyyhryg    360
kmdsgsrnnc rkvasmanad nvsmkrvgdy rggkkmyhgv vsvkgnkkad gsygcrgrra    420
svradycrys svdnnvymmr ravadrdrgk knshkvhdns gvnynvhdrm ahcahrvaaa    480
savwaaaaas vaahhraarg sggngagrhk rssagsasas ssvdssssha gsaagsssss    540
sgacgssasa gvaaagghhk aggsssssdsg arsaasagar ggghssrsss sgggsgagsr    600
svagasggas vgrggsghsg rsarasgshg sassvrrggr dksasadgar rashssgsma    660
aragggsggs gssggggryg aghvrksssgs sgarassgga grgarvrsks n            711

<210> SEQ ID NO 3
<211> LENGTH: 148
<212> TYPE: DNA
<213> ORGANISM: Human
<220> FEATURE:
<221> NAME/KEY: misc_feature
<222> LOCATION: (10)..(10)
<223> OTHER INFORMATION: n is a, c, g, t or u
<220> FEATURE:
<221> NAME/KEY: misc_feature
<222> LOCATION: (13)..(13)
<223> OTHER INFORMATION: n is a, c, g, t or u
<220> FEATURE:
<221> NAME/KEY: misc_feature
<222> LOCATION: (22)..(22)
<223> OTHER INFORMATION: n is a, c, g, t or u
<400> SEQUENCE: 3
tabsdmutan tsnkrwdtyh cntrdsvyta ardsvytrta artragmagm dsvytrkgmk     60
gmdsvytama rmdsvytaar dsgtrdsgvy atrdsavyrg tgdsvytraa aadsvyctrc    120
dsvystrsds vyttrtdsvy tragmagm                                       148
```